(12) United States Patent
Van Kuren et al.

(10) Patent No.: US 8,808,324 B2
(45) Date of Patent: Aug. 19, 2014

(54) HAND PRESSURE DEVICE TO DIMINISH GAG REFLEX RESPONSE

(75) Inventors: Michael Bailey Van Kuren, Hamilton, OH (US); Donna Scarborough, Cincinnati, OH (US)

(73) Assignee: Miami University, Oxford, OH (US)

( * ) Notice: Subject to any disclaimer, the term of this patent is extended or adjusted under 35 U.S.C. 154(b) by 481 days.

(21) Appl. No.: 12/471,857

(22) Filed: May 26, 2009

(65) Prior Publication Data
US 2009/0292228 A1 Nov. 26, 2009

Related U.S. Application Data

(60) Provisional application No. 61/055,490, filed on May 23, 2008.

(51) Int. Cl.
  A61B 17/00 (2006.01)
  A61H 39/04 (2006.01)
  A61H 39/00 (2006.01)
  A61B 17/132 (2006.01)
  A61H 7/00 (2006.01)

(52) U.S. Cl.
  CPC ............... *A61H 39/04* (2013.01); *A61H 39/00* (2013.01); *A61B 17/1325* (2013.01); *A61H 7/001* (2013.01); *A61H 2205/065* (2013.01)
  USPC .......................................... 606/201; 606/204

(58) Field of Classification Search
  CPC .. A61B 17/132; A61B 17/1325; A61H 39/00; A61H 39/002; A61H 39/007; A61H 39/02; A61H 39/04; A61H 2205/065; A61H 2201/165; A61H 7/001
  USPC ............ 606/201–204; 601/84, 134, 122–126, 601/46, 78, 79, 81, 97, 101, 107, 108; 607/2, 115; 600/15, 554; 310/23; 602/21, 22
  See application file for complete search history.

(56) References Cited

U.S. PATENT DOCUMENTS 4,173,218 A * 11/1979 Cronin ............................ 602/21
4,706,658 A * 11/1987 Cronin ............................ 602/13
(Continued)

FOREIGN PATENT DOCUMENTS

WO   WO 2006077572 A2 *  7/2006

OTHER PUBLICATIONS

Bartlett, Kenneth A.; Gagging. A Case Report; American Journal of Clinical Hypnosis, Jul. 1973; vol. 14, No. 1, pp. 54-56.

(Continued)

*Primary Examiner* — Darwin Erezo
*Assistant Examiner* — Katrina Stransky
(74) *Attorney, Agent, or Firm* — Yimei C. Hammond; Kremblas & Foster

(57) ABSTRACT

A method and device for reducing gag reflex by applying pressure to a pressure point in the palm of the hand. A splint that holds the hand relatively immobile has a rigid member and an actuating pressure system, such as a solenoid, at the pressure point. The rigid member at least partially immobilizes the human user's palm and fingers. The actuating pressure system is mounted at an inner side of the volar side of the enclosure adjacent to a pressure region of the palm. A power supply is connected to the actuating pressure system to apply an electrical current to the pressure system, which exerts pressure to the pressure region of the user's palm in order to diminish or normalize the user's gag reflex response.

25 Claims, 7 Drawing Sheets

(56) References Cited

U.S. PATENT DOCUMENTS

| | | | | |
|---|---|---|---|---|
| 5,067,478 | A * | 11/1991 | Berlant | 601/15 |
| 5,279,284 | A * | 1/1994 | Fenn | 601/108 |
| 5,405,357 | A * | 4/1995 | Rowe-Lanzisera et al. | 606/204 |
| 5,593,381 | A * | 1/1997 | Tannenbaum et al. | 601/93 |
| 5,709,647 | A * | 1/1998 | Ferber | 601/134 |
| 6,228,103 | B1 * | 5/2001 | Grey et al. | 606/204 |
| 6,361,550 | B2 * | 3/2002 | Grey et al. | 606/204 |
| 6,382,215 | B1 * | 5/2002 | Morrish | 128/898 |
| 6,582,449 | B2 * | 6/2003 | Grey et al. | 606/204 |
| 6,953,440 | B2 * | 10/2005 | Porrata et al. | 601/149 |
| 6,986,779 | B2 * | 1/2006 | Begley et al. | 606/204 |
| 7,087,029 | B2 * | 8/2006 | Friedland | 601/72 |
| 7,238,163 | B1 * | 7/2007 | Fried et al. | 601/122 |
| 2009/0112134 | A1 * | 4/2009 | Avni | 601/15 |

OTHER PUBLICATIONS

Bassi, G.S., et al.; The Etiology and Management of Gagging: A Review of the Literature; The Journal of Prosthetic Dentistry; May 2004; vol. 91, pp. 459-467.

Chaffee, Richard B., et al.; Suppression of the Gag Reflex by Exaggerated Respiratory Movements; Dent. Res. 1970; vol. 49, pp. 572-575.

Eitner, Stephan, et al.; Hypnopuncture—A Dental-Emergency Treatment Concept for Patients with a Distinctive Gag Reflex; Journal of Clinical and Experimental Hypnosis; 2005; vol. 53, pp. 60-73.

Eitner, Stephan, et al.; A Long-Term Therapeutic Treatment for Patients with a Severe Gag Reflex; International Journal of Clinical and Experimental Hypnosis; 2005; vol. 53. No. 1, pp. 74-86.

Fiske, J., et al.; The Role of Acupuncture in Controlling the Gagging Reflex Using a Review of Ten Cases; British Dental Journal; 2001; vol. 190. No. 11, pp. 611-613.

Kramer, Richard B., et al.; The Management of the Chronic or Hysterical Gagger; Journal of Dentistry for Children, 1977; vol. 44, pp. 111-116.

Landa, Joseph S.; Practical Full Denture Prosthesis; New York Dental Items of Interest Publishing Co., Inc.; 1947; pp. 268-279.

Leder, Steven B.; Gag Reflex and Dysphagia; Head & Neck publication; 1996; vol. 18, pp. 138-141.

Lu, Dominic P. et al.; Acupuncture/acupressure to Treat Gagging Dental Patients: A Clinical Study of Anti-Gagging Effects; General Dentistry; 2000; vol. 48, No. 4, pp. 446-452.

Miller, A.J.; Oral and Pharyngeal Reflexes in the Mammalian Nervous System: Their Diverse Range in Complexity and the Pivotal Role of the Tongue; Critical Reviews in Oral Biology & Medicine; 2002; vol. 13, pp. 409-425.

Murphy, W. M.; A Clinical Survey of Gagging Patients; The Journal of Prosthetic Dentistry; 1979; vol. 42, pp. 145-148.

Neumann, Joseph K., et al.; Behavioral Approaches to Reduce Hypersensitive Gag Response; The Journal of Prosthetic Dentistry; 2001; vol. 85. No. 3, p. 305.

Scarborough, D.R., et al.; Hypothetical Anatomical Model to Describe the Aberrant Gag Reflex Observed in a Clinical Population of Orally Deprived Children; Clinical Anatomy; 2006; vol. 19, pp. 640-644.

Scarborough, D.R., et al.; Abnormal Physiological Responses to Touch Among Children with Persistent Feeding Difficulties; Developmental Medicine & Child Neurology; 2006; vol. 48, pp. 460-464.

Vachiramon, Amornpong, et al.; Acupressure Technique to Control Gag Reflex During Maxillary Impression Procedures; The Journal of Prosthetic Dentistry; 2002; vol. 88, No. 2, p. 236.

Jacobs, Lawrence M.D., et al.; Three Primitive Reflexes in Normal Adults; Neurology; 1980; vol. 30, No. 2, pp. 184-188.

\* cited by examiner

HAND PRESSURE DEVICE TO DIMINISH GAG REFLEX RESPONSE

CROSS REFERENCES TO RELATED APPLICATIONS

This application claims the benefit of U.S. Provisional Application No. 61/055,490 filed on May 23, 2008, which is incorporated herein by reference.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

This invention relates to a hand pressure device to diminish a gag reflex response or to normalize a hypersensitive gag reflex response.

2. Description of the Related Art

The gag reflex regularly interferes with many medical procedures, more particularly, dental procedures. Most dental patients have suffered from the gag reflex when X-ray films or mold plaster is placed in the back of their mouth. As most victims know, the impulse to gag is uncontrollable and makes some dental procedures intolerable. This stimulation of the gag reflex can be a stressful time for the patient and the dentist. It can lead to delay of treatment where, for example, the patient is not able to complete X-ray or crown fitting procedures. The fear of discomfort and embarrassment from gag reflex keeps many patients from receiving regular dental care. Still other patients are not even able to adequately perform proper oral hygiene due to gagging, even during tooth brushing.

The gag reflex protects the airway against the entrance of unwanted material and triggers the contraction of the superior laryngeal muscles. In general the neurologic pathway for the gag reflex response involves the glossopharyngeal nerve (CN IX) which sends projection fibers from the posterior one-third of the oral cavity to the nucleus tractus solitarius (NTS) of the medulla. Information from the NTS then sends signals to the nucleus ambiguus (NA), which activates the vagal (CN X) efferent fibers to produce the specific motor response. Despite this rudimentary understanding of the gag reflex response pathway, the specific neurologic underpinnings are poorly understood.

Previous study results indicated that a typical gag response is triggered in the posterior one-third of the oral cavity within one of five trigger zones (Bassi G S, Humphris G M, Longman L P, J. Prosthet. Dent. 2004, v. 91, pp. 459-467). The five trigger zones are the anterior and posterior faucial pillars, the base of the tongue, the palate, the uvula and the posterior pharyngeal wall.

There is no clear definition of a hypersensitive gag reflex in a neurologically intact person. Instead, the description of a hyper gag reflex can be divided into two categories: The force of the motor response and the place of sensory stimulation.

The most common description involves the force of motor response. They include severely pulling away from tactile stimulation (Leder S B., Head Neck 1996, v. 18: pp. 138-141), spasms of the pharynx (Bassi G S, Humphris G M, Longman L P, J. Prosthet. Dent. 2004, v. 91, pp. 459-467) or a combination of reflex responses with both gagging and some aspect of the emetic response (Bassi G S, Humphris G M, Longman L P., J. Prosthet. Dent. 2004, v. 91, pp. 459-467; Kramer R B, Braham R L., ASDC 1977, v. 44, pp. 111-116; Miller A J., Crit. Rev. Oral Biol. Med. 2002, v. 13, pp. 409-425).

Another description of the hypersensitive gag reflex refers to the place of sensory stimulation, specifically where the gag reflex response is triggered. Historical reports of hypersensitive gagging incidents described people who triggered a gag reflex in the anterior or middle portions of the oral cavity during tooth brushing, while shaving, or after a touch to the face (Landa J S. Practical full denture prosthesis, New York: Dental Items of Interest Publishing Co., Inc., 1947, pp. 268-279; Murphy W. M., J. Prosthet. Dent. 1979, v. 42, pp. 145-148). Recently, gag reflex responses to non-oral body parts and regions within the anterior oral cavity have been documented in a group of children 3 to 18 months of age who had persistent feeding delays (Scarborough D R, Boyce S, McCain G, Oppenheimer S, August A, Neils-Strinjas J., Dev Med Child Neurol 2006, v. 48, pp. 460-464).

A hypothetical model of the specific neurologic cause of a hypersensitive gag reflex response has been proposed to explain the aberrant response to touch in regions other than the posterior one-third of the oral cavity in a group of orally deprived infants (Scarborough D. R., Isaacson L. G., Clin. Anat. 2006, v. 19, pp. 640-644). Based on this theory, 'transient' tactile connections between the touch sensory fiber tracts and the nucleus tractus solitarius (NTS) are present at birth via an inhibitory interneuron. The activity of the transient fibers diminishes shortly after birth as a result of swallowing during feedings. In a hypersensitive gag reflex response situation these transient fibers fail to retract and consequently result in continued stimulation of the NTS with touch to areas other than the posterior one-third of the oral cavity.

Attempts have been made to diminish the gag reflex response within clinical settings. Early interventions included swabbing patients' mouths with diluted cocaine; using distraction techniques; asking patients to use willpower (Landa J. S., Practical full denture prosthesis, New York, Dental Items of Interest Publishing Co., Inc., 1947, pp. 268-279); excising their uvulas (Kramer R B, Braham R L, ASDC 1977, v. 44, pp. 111-116); voluntarily increasing respiration (Chaffee R B, Zabara J, Tansy M F, J. Dent. Res. 1970, v. 49, pp. 572-575); holding their breath (Kramer R B, Braham R L, ASDC 1977, v. 44, pp. 111-116); hypnosis (Bartlett K A, Am. J. Clinical. Hypn. 1973, v. 1, pp. 54-56); and relaxing with hypnosis (Murphy W M, J. Prosthet. Dent. 1979, v. 42, pp. 145-148). Behavior modification, suggestion, systematic desensitization, sensory flooding and medications also have been explored (Bassi G S, Humphris G M, Longman L P., J. Prosthet. Dent. 2004, v. 91, pp. 459-467; Kramer R B, Braham R L., ASDC 1977, v. 44, p. 111-116; Neumann J K, J. Prosthet. Dent. 2001, v. 85(3), pp. 305).

Acupuncture points on the ear (Fiske J, Dickinson, C., Br. Dent. J. 2001, v. 190(11), pp. 611-613) or forearm (Lu D P, Lu G P, Reed J F, Gen. Dent. 2000, v. 48(4), pp. 446-452), can control the gag reflex effectively during dental treatments. Combinations of acupuncture and hypnosis were recommended to treat hypersensitive gag reflex responses during long-term therapies (Eitner S, Wichmann M, Holst S, J. Clin. Exp. Hypn. 2005, v. 53(1), pp. 74-86; Eitner S., Wichmann M., Holst S, J. Clin. Exp. Hypn. 2005, v. 53, pp. 60-73). Although this combination treatment may alleviate hyperactive gag reflex responses, complications may arise and specialized training or teams would be needed. Moreover, the invasive nature of the combination technique is undesirable for many patients. For most dentists and other medical practitioners, a less invasive approach, such as acupressure, would be an attractive alternative. However, even acupressure may require specialized training for it to be effective.

One brief clinical report has indicated that a pressure point on the chin would be effective for diminishing the gag reflex responses. However, no additional study was done to evaluate this pressure point (Vachiramon A, Wang W C, J. Prosthet. Dent. 2002; v. 88(2), p. 236).

In a study of abnormal physiological response to touch among children with persistent feeding difficulties, researchers found a link between feeding difficulties in children and abnormal response to touch using graded firm pressure (Scarborough D. R., Boyce S., McCain G., Oppenheimer S., Dev. Med. Child Neurol. 2006, v. 48(6), pp. 460-464). These abnormal responses included gagging and/or state changes at the anterior portion of the oral cavity or on non-oral parts of the body. From the results of the study, the researchers developed a published theoretical model to explain these abnormal responses (Scarborough D. R. & Isaacson, L. G., Clinical Anatomy, 2006, v. 19, pp. 640-644). According to this theoretical model, these abnormal response patterns have aberrant neurologic connections within the nucleus tractus solitarius of the brainstem.

BRIEF SUMMARY OF THE INVENTION

There exists a need for a device that reduces a person's gag reflex response without the need for specially trained personnel and without being invasive in situations such as dental procedures or examination. It is an objective of the present invention to provide a hand pressure device that can aid individuals with hyperactive gag reflex responses without any specialized trained personnel and without being invasive. The device can be safely and painlessly self-administered. It may also be portable and fully self-contained.

Embodiments of the invention address some or all of the concerns with the prior art. Products according to the invention are simple to manufacture and relatively inexpensive. Using the present invention, people have a diminished gag reflex response during dental procedures without the assistance of any specially trained personnel and without being unduly invasive.

The present invention comprises an enclosure with at least one substantially rigid member and an actuating pressure system. The rigid member is adapted to at least partially immobilize a human user's palm and at least a portion of the user's fingers. The actuating pressure system is mounted at an inner side of the volar side of the enclosure adjacent to a pressure region of the palm. A power supply is connected to the preferred actuating pressure system to provide an electrical current to the actuating pressure system to exert pressure against the pressure region of a user's palm in order to diminish or normalize the user's gag reflex response.

The pressure region is a 1.5 inch diameter region around a pressure point located at a middle of the palm at an intersection of two straight lines perpendicular to each other. One of the lines extends from a middle of a volar distal edge of an intermediate phalange of a third finger to the middle of the palm, and the other line extends from a middle of a proximal phalange of a thumb to the middle of the palm. Preferably, the pressure region is a 1.5 inch, or more preferably a 0.5 inch, bell curve fading from each direction of the pressure point. Most preferably, the pressure region coincides substantially with the pressure point.

In a preferred embodiment, the enclosure is a splint adapted to conform to a palm region of the user's hand and to extend over at least one portion of the user's fingers. The splint includes a volar member, a dorsal member, and an optional opening at the volar member of the splint sized to allow the pressure system to be removably mounted in the opening. The actuating pressure system includes a voice coil actuator and a pressure cylinder attached to one end of the voice coil actuator. The pressure cylinder protrudes slightly out of the inner side of the volar member adjacent to the pressure region of the palm. Alternatively, the pressure system is mounted at an inner surface of the volar member adjacent to the pressure region of the palm.

Preferably, the voice coil actuator is a solenoid capable of converting electrical energy into linear motion so as to actuate the pressure cylinder. Further, the solenoid is preferably capable of both precise force control and being used in short stroke, close loop servo applications. Optimally, the solenoid is capable of actuating a peak force of at least about 2 lbs.

The splint includes a knuckle strap adapted to immobilize the fingers and a wrist strap with a fastener system to attach the splint to a wrist or a lower portion of the hand to provide support to the device.

A preferred method of using the present invention includes: (a) providing an embodiment of a hand pressure device of the present invention for reducing gag reflex response; (b) fitting the hand pressure device onto a hand of a user; (c) positioning the actuating pressure system so that it is able to exert pressure to the pressure region of the palm; and (d) applying an electrical current to the actuating pressure system to exert pressure to the pressure region so as to reduce the user's gag reflex response. Preferably, step (c) further comprises increasing the pressure exerted onto the pressure region to at least about 0.5 lbs. More preferably, the method further includes a step of stopping the application of the force to the pressure region of the palm for fifteen to thirty minutes and then a subsequent step of reapplying an electrical current to the actuating pressure system to exert pressure on the pressure region.

Alternatively, the method of using a hand pressure device for altering gag reflex includes: (a) providing an embodiment of a hand pressure device of the present invention for reducing gag reflex response; (b) positioning an actuating pressure system so that it is adjacent a pressure region on the volar side of a user's hand; (c) securing the actuating pressure system to the palm using one or more straps; (d) mounting the actuating pressure system onto the inner surface at the volar side of the enclosure; (e) fitting the hand pressure device onto the hand; (f) securing the device to the hand through one or more straps; and (g) applying an electrical current to the actuating pressure system to exert pressure to the pressure region so as to reduce the user's gag reflex response. More preferably, the method further includes a step of stopping the application of the force to the pressure region of the palm for fifteen to thirty minutes and then a subsequent step of reapplying an electrical current to the actuating pressure system to exert pressure on the pressure region.

This brief summary has been provided so that the nature of the invention may be understood quickly. A more complete understanding of the invention may be obtained by reference to the following description of the preferred embodiments thereof in connection with the attached drawings.

Figure 1:
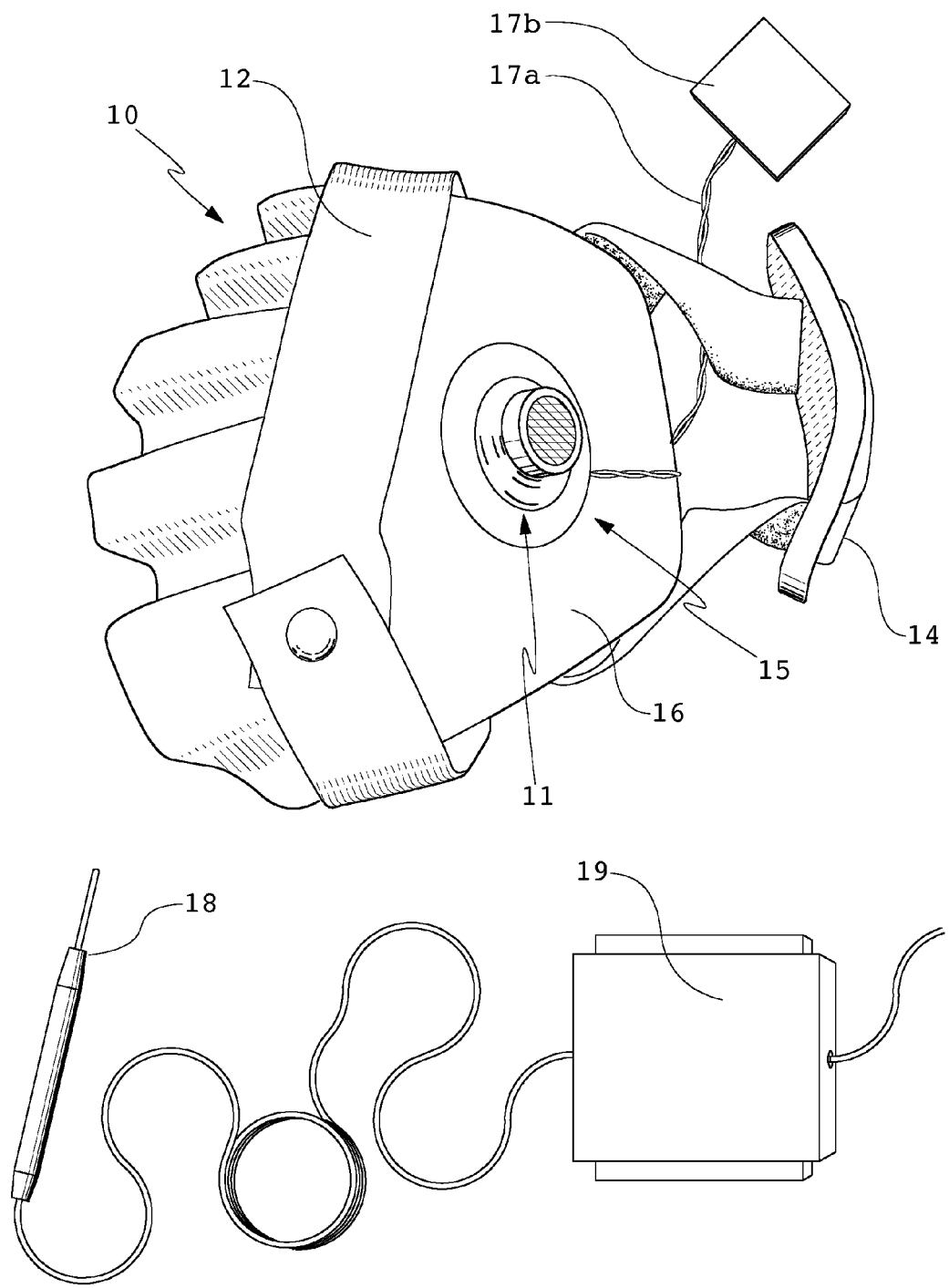
FIG. 1 is a top perspective view illustrating a preferred embodiment combined with a test probe used for sensing oral gag reflex response and a data collecting device for collecting information from the test probe and the preferred embodiment. The test probe and the data collecting device are not a part of the preferred embodiment, and were used to collect study data in example 3.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DETAILED DESCRIPTION OF THE INVENTION

Broadly speaking, the present invention is a hand wearable pressure device used to normalize or diminish gag reflex responses in a human who is wearing the device. A preferred embodiment of the present invention has three main parts— an enclosure with at least one substantially rigid member, an actuating pressure system ("pressure system") that includes several sub-components, and a power supply. In practice, some or all components of the pressure system and the power supply can be removed from the enclosure for washing, storage or other purposes. In use, the enclosure is placed on a user's hand, and the pressure system applies pressure as powered by the power supply to a pressure region of the user's palm. This pressure has been shown to reduce the human gag reflex response in people prone to excessive response.

A pressure region 41 (see FIG. 4) is a region on the human hand that is a 1.5 inch radius, generally circular, region around a pressure point 42 that is located at a middle of the palm 43. The pressure point 42 is located at an intersection of two straight lines that are substantially perpendicular to each other. One line extends vertically (in the FIG. 4 orientation) from a middle of a volar distal edge of an intermediate phalange of a third finger to the middle of the palm 43. The other line extends horizontally (in the FIG. 4 orientation) from a middle of a proximal phalange of a thumb to the middle of the palm 43. Preferably, the pressure region 41 is a 1.5 inch, or more preferably a 0.5 inch, bell curve fading from each direction of the pressure point 42 on the palm 43. Most preferably, the pressure region 41 coincides substantially with the pressure point 42.

Figure 3:
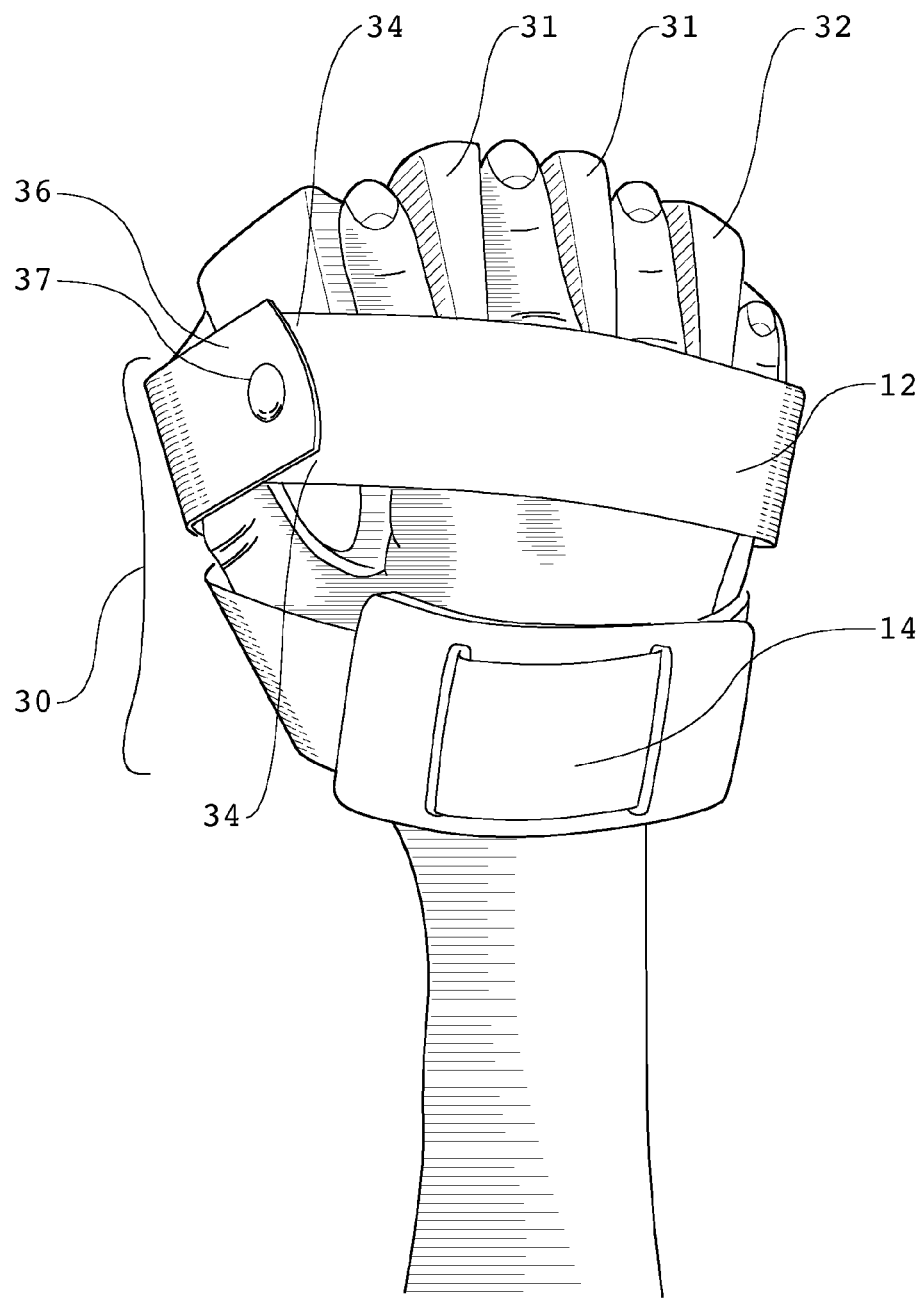
FIG. 3 is a dorsal view illustrating a preferred embodiment as illustrated in FIGS. 1 and 2, showing a dorsal side of the device with a wrist strap and a knuckle strap to immobilize fingers, wherein the device is shown to be operatively associated with a human hand.

In a preferred embodiment, the enclosure is a splint 10 formed to accept the hand and fingers of any normal human. The splint 10 may optionally be modifiable for a custom fit. The splint 10 is removably attached to the hand as shown in FIG. 3, preferably by the straps 12 and 14. Of course, more or fewer than two straps can be used.

Figure 2:
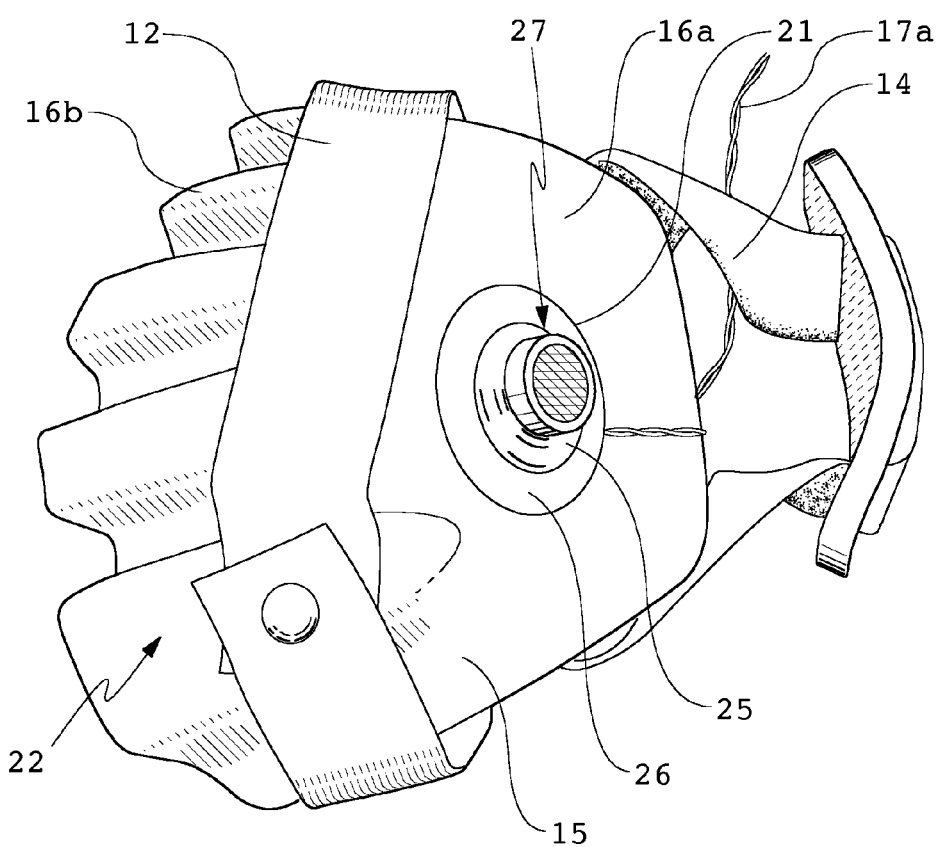
FIG. 2 is a volar view illustrating a volar side of the preferred embodiment as illustrated in FIG. 1, showing a volar side of the device and an actuating pressure system mounting in an opening at the volar side of the device.

The splint 10 generally includes a volar member 15 (FIG. 2) and a dorsal member 30 (FIG. 3). When in use as shown in FIG. 3, the volar member 15 is positioned adjacent a volar side of the wrist, palm and fingers. The volar member 15 extends from a first, proximal end of the splint 10 at or near the beginning of the wrist 45 to a second, distal end at or near the ends of fingers 44. The dorsal member 30 is positioned adjacent a dorsal side of the wrist, the palm and the fingers. The dorsal member 30 extends from a first, proximal end of the splint 10 at or near the beginning of the wrist 45 to a second, distal end of the splint 10 at or near the ends of the fingers 44. In general, the human hand is inserted between the volar member 15 and the dorsal member 30 when in use, as shown in FIG. 3, thus positioning the volar member 15 on the palm side of the hand, and the dorsal member 30 on the dorsal side of the hand.

The volar member 15 and the dorsal member 30 are preferably attached to each other (permanently or removably) through the straps 12 and 14, or other suitable attachment structures. In the preferred embodiment, the flexible fabric straps 12 and 14 form part of the dorsal member 30, and also extend between the dorsal member and the volar member to attach the two, thereby allowing for flexible interconnection of the volar and dorsal members 15 and 30. The straps 12 and 14 also aid in clamping the wrist 45, hand 40, and fingers 44 between the volar member 15 and the dorsal member 30.

The volar member 15 preferably includes at least one rigid palm member 16, which in the preferred embodiment is at least the central region of the splint 10 surrounding the pressure system (described below). The rigid member 16 is formed of a material possessing a high degree of inherent rigidity which, once it has received its configuration, cannot subsequently be deformed any more without applying substantially more force than a typical human hand can apply. Preferably, the volar member 15 also includes a soft material (not shown) to provide padding to the rigid member 16, and/or a cover (not shown) to enclose both the rigid member 16 and the soft material. The padding can be a closed cell foam or an open cell foam. The cover encloses both the soft padding material and the rigid member and is positioned adjacent the skin of a user. Such a cover could be removed for cleaning or disposal. Alternatively, the open cell foam layer can be positioned adjacent the skin of a user for more enhanced comfort.

The rigid member 16 portion of the volar member 15 more preferably extends the entire length and width of the volar member 15, including at least a palm support region 16a and a volar finger support region 16b. The palm support region 16a and the volar finger support region 16b support the hand parts after which they are named. The palm support region 16a can be substantially planar, but is more preferably convex, to support the hand at a natural angle for use in the present invention to withstand the pressure exerted by the cylinder system 11 as described below. Other configurations of the palm support region 16a are also contemplated so long as they enhance immobilization of the user's palm to enable the device to apply pressure to the pressure region 41 consistently in order to reduce the user's gag reflex response.

The finger support region 16b extends from the palm support region 16a. The finger support region 16b can be substantially planar or can have a convex shape, especially a shape that continues the shape of the palm support region 16a. The angle of the finger support region in relation to the palm support region may be any suitable angle for proper positioning of the fingers for withstanding the pressure exerted by the pressure system 11 and to enable the pressure system 11 to exert consistent pressure on the pressure region 41 of the palm. Further, the finger support region 16b preferably has a plurality of elongated ribs or protrusions 31 spaced apart to define grooves therebetween into which fingers 44 are placed to keep the fingers 44 spread apart. Alternatively, the splint 10 may comprise separate projections adjacent each finger, and the rigid member 16 extends distally into each projection to stabilize or immobilize the fingers 44. It is currently believed that spreading or immobilizing fingers may assist in stabilizing the palm to enable the present invention to apply consistent pressure to the pressure region of the palm to reduce a user's gag reflex response.

A preferred splint for use with the present invention is a modified version of the D. Rolyan® Hand-Based Anti-spasticity Ball Splint from Sammons Preston Rolyan. However, any suitable splint or equivalent structure can be used. The splint 10 is preferably formed so that all of the subject's fingers, including the thumb, rest comfortably in a curved position. The splint 10 may be formed for the left or right hands.

The dorsal member 30 preferably has multiple straps 12 and 14 to secure the splint 10 to the hand and thereby immobilize and stabilize the palm and fingers by clamping them to the preferably rigid volar member 15. Optionally, the dorsal member 30 can further include a rigid dorsal support (not shown) to seat against the dorsal portion of the hand and the fingers. This dorsal support further stabilizes the palm to ensure that a consistent pressure is applied to the pressure region 41 of the palm 43, more preferably, to the pressure point 42, in order to reduce the user's gag reflex response.

Referring to FIG. 3, one end 34 of the knuckle strap 12 is secured to the finger support region 22 between the grooves formed in the splint 10 for the thumb and the first forefinger. The other end 36 of the knuckle strap 12 is attached to the fixed end 34 using a snap fastener system 37. One end (not shown) of the wrist strap 14 is secured to the rigid member 16, and the opposite end (not shown) is similarly, but adjustably, attached to the rigid member 16 on the opposite lateral side of the rigid member 16. Of course, the straps 12 and 14 can be attached to any portion of the rigid member 16 as long as they fix the fingers to the splint 10.

The knuckle strap 12 and wrist strap 14 are preferably non-elastic and secure the hand to the splint 10 by wrapping around the respective dorsal regions of the hand as shown in FIG. 3. Two distal ends of the wrist strap 14 are fixedly or removably attached to two edges of the volar member 15 at the lower portion of the palm support region. Two proximal ends of the strap 14 are fastened to each other through a buckle fastening system. Specifically, one free proximal end is fastened through a buckle (not shown) attached near the other end of the strap 14. Although a buckle fastener is preferred for its ease of use, other manners of fastening may be employed within the scope of the present invention, such as a hook and loop type fastening system. Additional straps may also be used to assist in immobilizing the palm and fingers.

The dorsal region between the straps 12 and 14 and above the first strap 12 preferably has no covering to enclose the dorsal side of the hand when the device is in use. Alternatively, this space can be covered by a plate or another strap if a more secure hand-securing means is desired.

The splint 10 is thus preferably designed to at least partially immobilize the user's palm 43 and fingers 44 when the hand is inserted in an operable manner. The preferred structure enables the pressure system 11 (see FIG. 1) to exert an appropriate and consistent amount of force on the pressure region 41 of the palm 43 without substantial movement of the fingers and/or the palm away from the rigid member 16, which is preferably the entire volar member 15. Movement of the palm 43 and the fingers 44 might otherwise change the pressure applied or move the pressure system 11 away from the pressure region 41 of the palm 43.

The pressure system 11 can be any suitable mechanical device that can apply pressure to the palm of a user's hand. Preferably, the pressure system 11 is a solenoid that is capable of converting electromagnetic energy into linear motion to actuate a pressure force on a pressure region of a human user's palm. Of course, other mechanical devices, including but not limited to pneumatic and/or hydraulic bladders and bellows, piezoelectric crystals and other devices can be substituted for the preferred solenoid. Such devices differ in size to the system used, and therefore may not require an opening to be formed through the rigid member 16 in order to be fitted in the splint 10 to exert pressure on the pressure region of the palm.

The pressure system 11 is preferably mounted at an inner surface 55 (see FIG. 5) of the volar side of the splint 10 adjacent to the pressure region 41 of the palm 43. More preferably, the pressure system 11 includes a voice coil actuator 27 and a pressure cylinder 28 attached to one end of the voice coil actuator 27.

Figure 5:
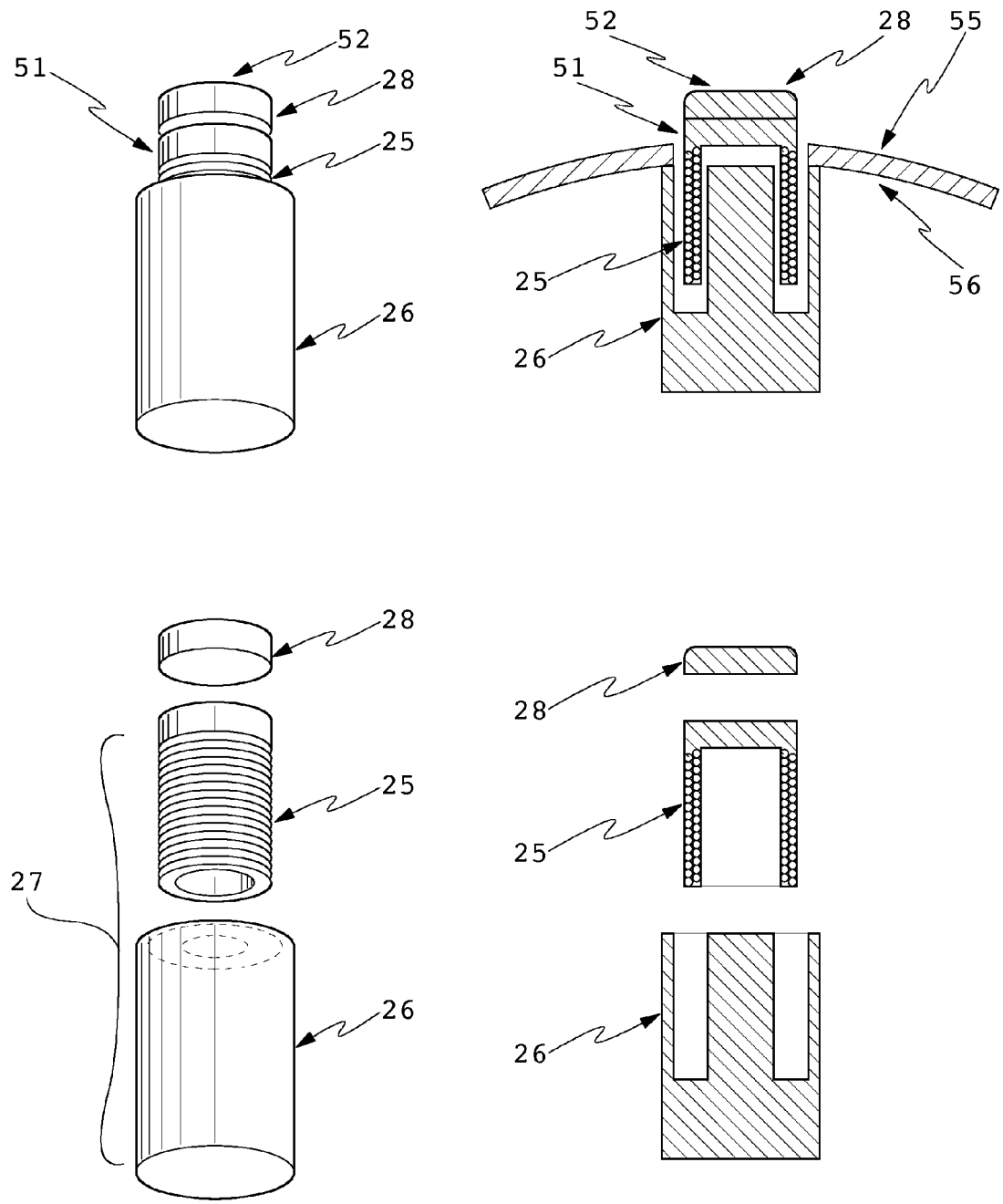
FIG. 5 is an exploded perspective view of an actuating pressure system mounting in an opening on the volar member of the enclosure in an embodiment as illustrated in FIGS. 1 and 2.

Most preferably, the pressure system 11 is removably, but can be permanently, mounted in an opening 21 on the volar member 15 of the splint 10 (see FIG. 5). The inner end 52 of the pressure cylinder 28 protrudes slightly out of the inner surface 55 of the volar member 15 at the palm support region 16a. This slight protrusion of the inner end 52 enables the user to identify in a tactile manner whether the inner end 52 of the pressure cylinder 28 is appropriately positioned against the pressure region 41 of the palm 43, and if necessary, to adjust the splint 10 to position the pressure cylinder 28 against the pressure region 41.

The pressure cylinder 28 attaches to the volar member 15 of the splint 10 through an interference fit or any other suitable attachment means. The voice coil actuator 27 protrudes out of an outer surface 56 of the volar member 15 of the splint 10. One or more power leads 17a extend from the voice coil actuator 27 to a power supply 17b.

Figure 6:
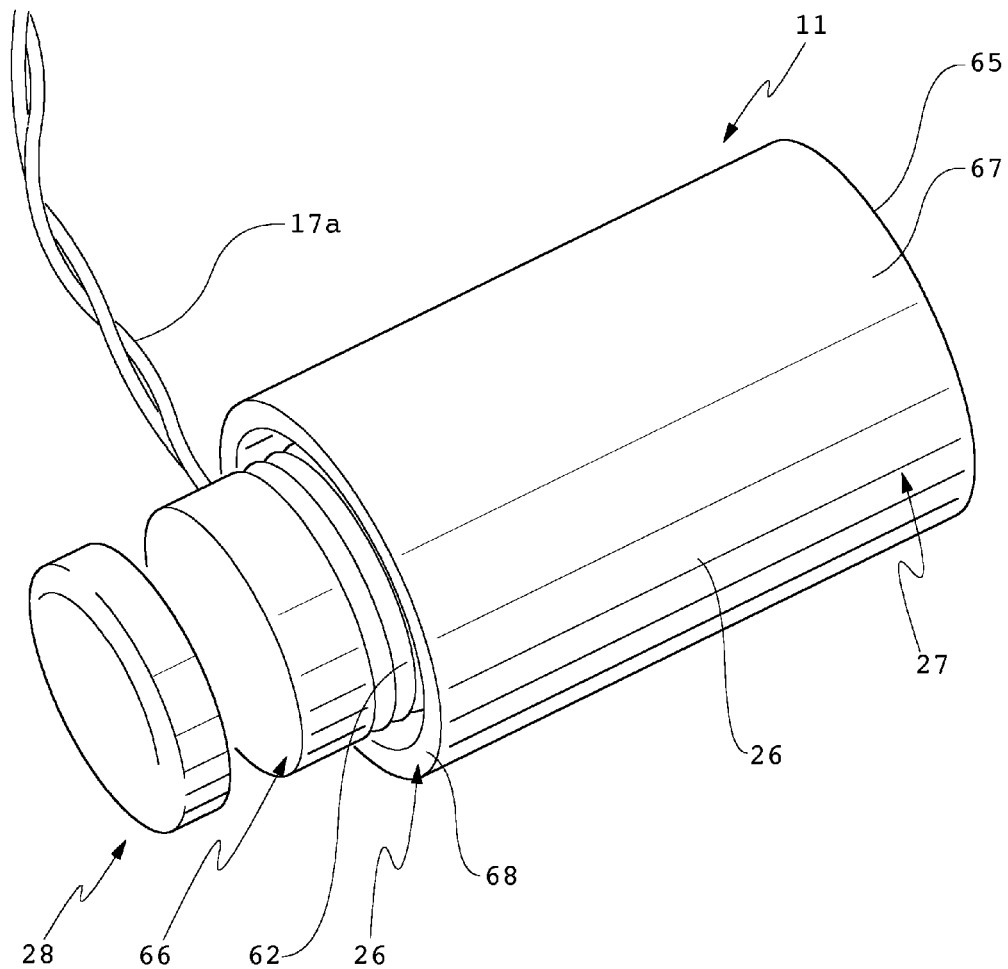
FIG. 6 is a side perspective view illustrating an actuating pressure system in a preferred embodiment as illustrated in FIGS. 1 and 2.

The voice coil actuator 27 includes a coil component 25 and a housing 26. As shown in FIG. 6, the coil component 25 includes a coil 62 and one or more permanent magnets (not shown). The housing 26 is formed of magnetically permeable material and has an upper end 67 and a lower end 68. Other mechanical links from the coil component 25 to the load can be employed, such as the holes or slots through the actuator ends 65 and 66.

The pressure cylinder 28 is formed of plastic or other suitable material so that it has minimum weight but is rigid enough to exert pressure to the palm. Preferably, the pressure cylinder 28 is about 1.0 inch in length and about 1.2 inches in diameter. An outer end 51 of the pressure cylinder 28 is attached to a lower end of the coil component 25 through two screws, transforming the coil 62 from a moving coil to the fixed coil component 25. The moving part of the voice coil actuator 27, the housing 26, floats above the fixed coil component 25 and is not attached to the pressure cylinder 28, thereby permitting it to float relative to the fixed coil component 25 and the plastic pressure cylinder 28.

A preferred voice coil actuator 27 for use with the present invention is a modified version of the moving coil actuator, NCC05-11-011-1X, produced by H2W Technologies, Inc. However, any suitable voice coil or solenoid may be used as long as it is capable of precisely controlling the conversion of energy into linear motion to apply a desired pressure to the pressure region 41. Unlike the original moving coil actuator NCC05-11-011-1X, where the coil is the moving part and the housing is the stationary part, in the modified version of the actuator the fixed coil component 25 and the housing 26 move along the fixed coil component 25.

The actuator 27 is preferably capable of being used in short stroke (typically less than 2 inches) closed loop servo applications. More preferably, the actuator 27 should have a compact size so as to allow it to fit into the small opening 21 on the volar member 15 of the splint 10. The actuator's low electrical and mechanical time constants translate to a low moving mass, which allows for high acceleration of light payloads. Most preferably, the modified version of NCC05-11-011-1X voice coil actuator is a moving house actuator capable of a 0.50 inch stroke, 1.10 lbs of continuous force, 3.30 lbs peak force, and 0.67 Km lbs/(watt)$^{0.5}$ with one pole magnet assembly, a 1.20 inch outside diameter, and a 1.10 inch housing length.

In the preferred embodiment, the actuator 27 is coupled to a bearing system (not shown), a position feedback device (not shown), a DC linear servo amplifier (not shown) and a motion controller (not shown), yielding a system that is capable of precise force control, such as intricate positioning, velocity and acceleration. The actuator 27 preferably operates on the principal of the Lorentz Force Equation: Force=B×I, where B=Flux density (Tesla) and I=Current (Amps). Simply stated, a current carrying conductor placed in a magnetic field will have a force exerted upon it, which is proportional to the direction and magnitude of the current and the flux density field. Since the permanent magnet flux density field is fixed, the direction of the linear displacement depends on the polarity of the input current. Accordingly, the amount of force that is produced is directly proportional to the magnitude of the input current.

The power source 17b is electrically connected to the pressure system 11 through power leads 17a to provide an electrical current to the pressure system 11 to enable the pressure system 11 to exert pressure to the pressure region 41 of the palm 43. Preferably, the power supply 17b is connected to the voice coil actuator 27 of the pressure system 11. Alternatively, a control system that actuates the voice coil actuator 27 can be connected to the pressure system 11 through a wireless system instead of using a wired connection.

The power supply 17b can be located separately from, adjacent to, or integral with, the cylinder system 11. The power supply 17b can be any power source that allows for manual, and preferably variable, control of the power supplied to the actuator 27, in order to thereby control the force applied to the user's hand. Preferably, the power supply is a bipolar operational power supply, which also includes an amplifier. It is also contemplated that a portable and lightweight power supply can be used, such as a photovoltaic cell, a fuel cell, etc., as long as it allows for manual and preferably variable control of the force applied to the pressure region 41 of a user's palm. This control of the applied force can be accomplished by adding a control feature to the power supply, such as a micro controller.

Methods of using the present invention vary. A preferred method includes the following steps: (1) placing the straps 12 and 14 in a loosened position or completely disengaged from interaction with the volar member 15; (2) inserting the user's hand 40 into the splint 10 with his or her palm facing the volar member 15; (3) positioning the pressure system 11 so that the pressure system 11 is lightly touching the pressure region 41 of the palm, preferably touching the pressure point 42; (4) positioning the fingers 44 in the grooves between appropriate protrusions 31 on the dorsal finger support region; (5) tightening the straps 12 and 14 to securely fasten the splint 10 to the hand 40; and (6) applying an electrical current to the pressure system 11 to exert pressure to the pressure region 41 of the palm, preferably to the pressure point 42 of the palm. The pressure exerted onto the pressure region should be at least about 0.5 lbs. More preferably, the method further includes a step of stopping the application of the force to the pressure region 41 of the palm for fifteen to thirty minutes and then a subsequent step of reapplying an electrical current to the pressure system to enable it to exert another pressure force on the pressure region 41. While not wishing to be bound by theory, it is currently believed that the stopping of pressure for fifteen or thirty minutes might not create a gap in, or otherwise reduce, the effectiveness of the device to diminish gag reflex responses. It is believed that this occurs because the pressure treatment might be effective within fifteen to thirty minutes of halting the application of pressure.

Alternatively, a preferred method of using the present invention includes the following steps: (1) positioning the pressure system 11 so that the pressure system 11 is lightly touching the pressure region 41 of the palm; (2) securing the pressure system 11 to the palm 43 with one or more straps or other appropriate fastening devices; (3) mounting the pressure system 11 in the opening 21 of the splint 10 with loosened straps 12 and 14; (4) fitting the splint 10 over the hand; (5) tightening the straps 12 and 14 to securely fasten the splint 10 to the hand 40; and (6) applying an electrical current to the pressure system 11 to exert pressure to the pressure region 41 of the palm, preferably to the pressure point 42 of the palm. Preferably, the pressure exerted onto the pressure region should be at least about 0.5 lbs. More preferably, the method further includes a step of stopping the application of the force to the pressure region of the palm for fifteen to thirty minutes and then a subsequent step of reapplying an electrical current to the pressure system 11 to enable the pressure system 11 to exert another pressure force on the pressure region.

The present invention is further illustrated by the following examples which are illustrative of some embodiments of the invention and are not intended to limit the scope of the invention in any way.

Previous study results indicated that a typical gag response is triggered on the posterior one-third of the oral cavity within one of five trigger zones (see background for the definition of the five trigger zones) (Bassi G. S., Humphris G. M., Longman L. P., J. Prosthet. Dent. 2004, v. 91(5), pp. 459-467). This region is innervated by the glossopharyngeal nerve, which is the afferent limb for the gag reflex.

The prior study on children with persistent feeding difficulties (Scarborough D. R., Boyce S., McCain G., Oppenheimer S., Dev. Med. Child Neurol. 2006, v. 48(6), pp. 460-464) prompted the researchers to explore the effect of contact with various parts of the body on reducing feeding difficulties of the children, or in the alternative, reducing children's abnormal response to contacts. Through clinical trials and errors, the researchers found that applying some pressure on a pressure point in the palm of a child's hand might remediate the hypersensitivity to touch somewhat on both oral and non-oral part of the body in children with feeding difficulties (Scarborough, D., Bailey-Van Kuren, M., Hughes, M., J. Am. Dent. Assoc. 2008, v. 139, p. 1366). However, the researchers did not develop a consistent methodology to use this technique for a clinical setting, nor did they substantiate the technique's efficacy in reducing gag reflex response.

Figure 7:
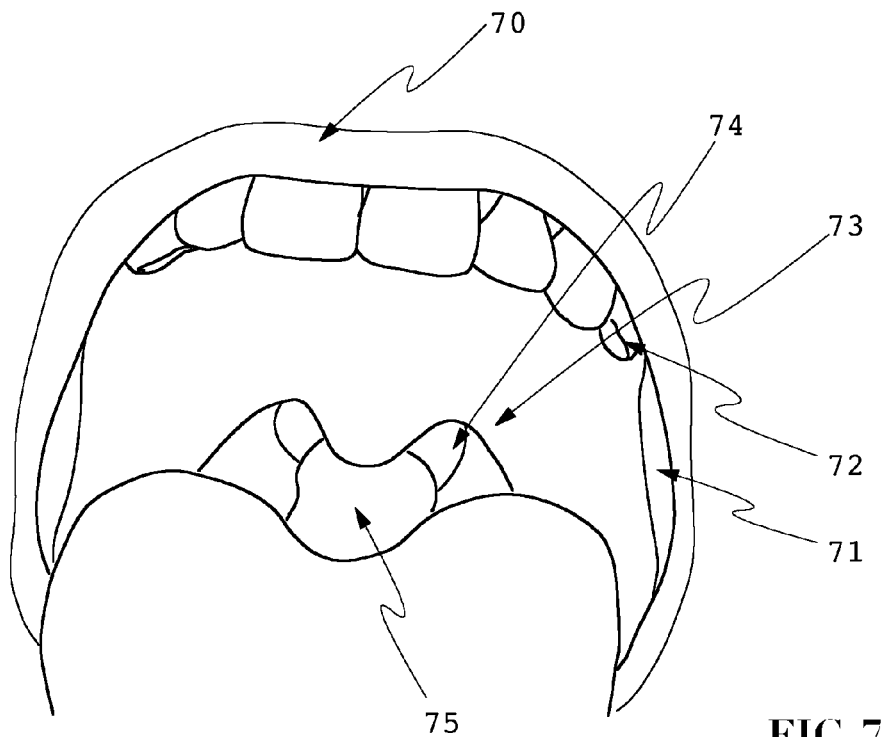
FIG. 7 is a front perspective view illustrating key landmarks of the gag trigger point index (GTPI) in an oral cavity.

In the following examples, the subjects were placed into the hypersensitive group if they gagged when they received stimulation in more anterior regions, such as at or before the anterior faucial pillar 73 as illustrated in FIG. 7. Other subjects were placed into the normal sensitivity group (normal group).

Example 1

This Example is an informal pilot study developed to study the effect of putting pressure on the pressure point of a human palm on adults with a hypersensitive gag reflex response.

Subjects:

This study tested five human subjects with a hypersensitive gag reflex response, all of whom had an intact neurological system. Of the five subjects, three were women and two were men. Four of the subjects were white and one was African-American.

Procedure:

Baseline trials were performed by eliciting two gag reflex responses: one gag reflex response at the left side of the oral cavity and another gag reflex response at the right side of the oral cavity. After the baseline data were collected, a pressure was applied to the pressure point on the palm of a randomly selected hand. The subject's gag reflex response was elicited during the pressure application.

Results:

In four subjects, the point in the mouth at which stimulation elicited a gag reflex response moved posteriorly to the posterior pharyngeal wall 70 (see FIG. 7) after a pressure treatment on the pressure point of the palm. Of these four subjects, two of them had a baseline of gagging at the internal cheek 71 while the other two subjects had a baseline of gagging at the second molars 72. The fourth subject, the African American male, showed no change in the position of the gag reflex response in the oral cavity after the pressure treatment.

Conclusion:

The pressure treatment on the pressure region of the palm caused normalization (that is, triggering the gag reflex in the posterior portion of the oral cavity) in all of the subjects except for the African American male. While not wishing to be bound by theory, it is presently believed that the pressure might have been applied to an incorrect point on the palm of the African American male because of the size of the subject's hand More extensive studies will need to be completed to test the theory.

Example 2

Example 1 lead to this second pilot study to develop consistent methodological techniques to apply in a larger sample.

Subjects:

Seven healthy white women with hypersensitive gag reflex responses were tested. The subjects were determined to have a hypersensitive gag reflex because the gag was triggered in the anterior two-thirds of the oral cavity.

Figure 4:
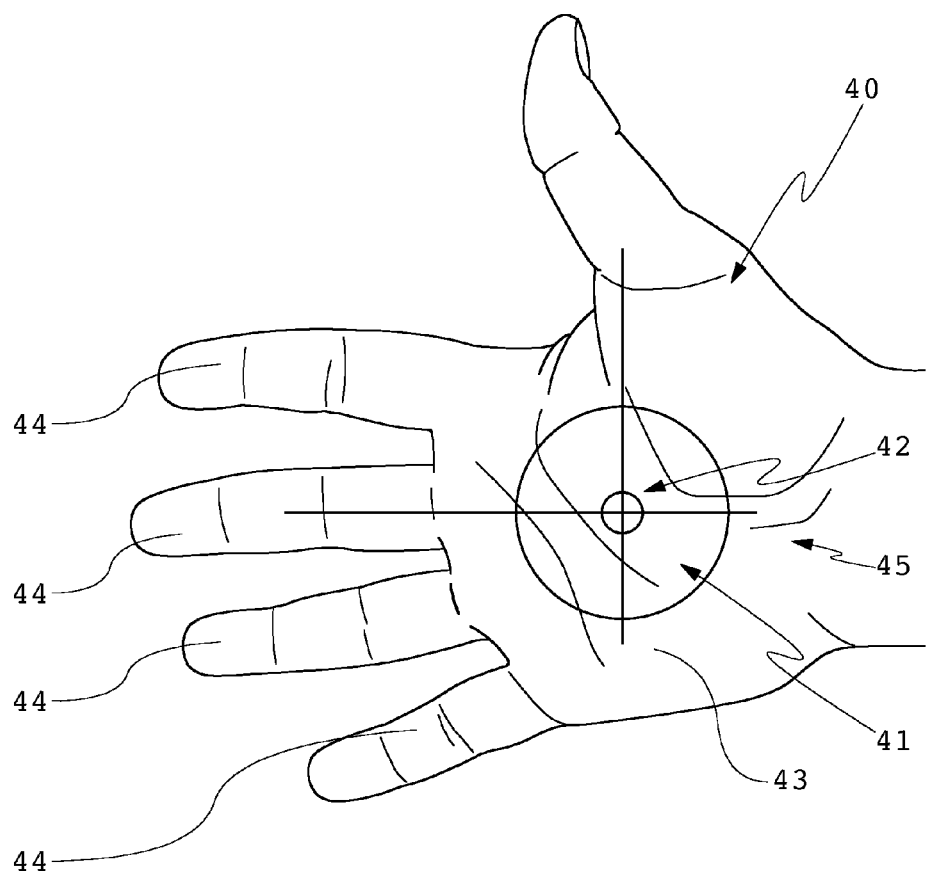
FIG. 4 is a volar perspective view illustrating a pressure region and a pressure point on a palm of a human hand.

Procedure:

Marked both hands of each subject at the pressure point 42 where the middle aspect of the thumb and the third finger intersect as shown in FIG. 4. Baseline trials were then performed by eliciting two gag reflex responses with one gag reflex response on the left side of the oral cavity and another gag response at the right side of the oral cavity. The severity of the gag was rated and the baseline data was collected. Once the baseline data was collected, a randomly selected hand of the subject was secured in a clamp system with the palm facing upward. The clamp had a pointed force probe on one end and a flat base. The pointed probe was aligned with the marked pressure point 42 and included a force sensitive resistor to enable an investigator to provide force to the probe. The force probe was manually adjusted to apply pressure until the reading registered between 0.5-1.0 pounds of force. The subject's hand remained in the clamp system while her gag reflex response was tested bilaterally. After the first gag reflex data was collected, the other hand was then placed in the clamp system, and the force probe was manually adjusted to apply pressure to 0.5-1.0 pounds while the gag reflex response was again assessed bilaterally.

The gag reflex response was elicited using a standard wooden disposable tongue blade for each test. In eliciting a gag reflex, the tongue blade was directed posteriorly and angled vertically to avoid the base of the tongue. The anatomic landmark was recorded when a gag reflex response was triggered while an appropriate pressure was applying to the marked pressure point of the palm. At least one minute "rest" period was provided between eliciting gag reflexes to minimize any potential extinction or fatigue effect.

Two subjects were used to examine the length of the post-pressure effect, that is, how long the effect of the pressure application to the palm would last after the pressure application has stopped. For one subject a pointed tip probe was used while a standard probe tip was used on the other subject. A pressure was applied to the marked pressure point of the subjects' palm for approximately two minutes. The gag reflex responses of the subjects were then measured at five, fifteen, and thirty minutes after the ending of the pressure application to the palm.

Results:

Table 1 lists the baseline data (without applying any pressure to the marked pressure point of the palm). Table 2 lists the gag reflex response data for the application of 0.5-1.0 lbs pressure to a right hand of the subjects. Table 3 lists the gag reflex response data for the application of 0.5-1.0 lbs pressure to a left hand of the subjects. In Tables 1-3, if a gag reflex response was elicited at the right side of the oral cavity, an "x" was marked in the table for an appropriate anatomical landmark for that subject; if a gag reflex response was elicited at the left side of the oral cavity, an "o" was marked in the table for an appropriate anatomical landmark for that subject. For the purpose of this example, if a gag reflex response was elicited at or after posterior faucial pillar, that subject was considered to have a normal gag response. Accordingly, if a gag response was elicited at or before anterior faucial pillar, the subject was considered to have a hypersensitive gag reflex response.

In studying the effect of the post pressure application period, a return of hypersensitivity gag reflex response was found between 15 and 30 minute trials for both subjects.

TABLE 1

Gag Response Data of the Baseline Trial

| | Anterior to Cheek/Cheek | 12-yr Molars | 12-ys Molars/Ant. Faucial Pillars | Ant. Faucial Pillars | Ant. Faucial P./Post Faucial P. | Post. Faucial Pillars* | Post. Faucial Pillars/ Post Pharyngeal Wall | Post. Pharynx Wall |
|---|---|---|---|---|---|---|---|---|
| Subject 1 | | x, o | | | | | | |
| Subject 2 | | | x | o | | | | |
| Subject 3 | x, o | | | | | | | |
| Subject 4 | | X | o | | | | | |
| Subject 5 | | | x | o | | | | |
| Subject 6 | | | x | o | | | | |
| Subject 7 | | | x | o | | | | |

TABLE 2

Gag Response Data following the Application of 0.5-1.0 lbs. Pressure to Right Hand

| | Anterior to Cheek/Cheek | 12-yr Molars | 12-ys Molars/Ant. Faucial Pillars | Ant. Faucial Pillars | Ant. Faucial P./Post Faucial P. | Post. Faucial Pillars* | Post. Faucial Pillars/ Post Pharyngeal Wall | Post. Pharyn Wall |
|---|---|---|---|---|---|---|---|---|
| Subject 1 | | | | | | o | | x |
| Subject 2 | | | | | | x, o | | |
| Subject 3 | | | x, o | | | | | |
| Subject 4 | | | | | | x, o | | |
| Subject 5 | | | | | | | x | o |
| Subject 6 | | | | | | x, o | | |
| Subject 7 | | | | x | | o | | |

TABLE 3

Gag Response Data Following the Application of 0.5-1.0 lbs. Pressure to Left Hand

| | Anterior to Cheek/Cheek | 12-yr Molars | 12-ys Molars/Ant. Faucial Pillars | Ant. Faucial Pillars | Ant. Faucial P./Post Faucial P. | Post. Faucial Pillars* | Post. Faucial Pillars/ Post Pharyngeal Wall | Post. Pharyn Wall |
|---|---|---|---|---|---|---|---|---|
| Subject 1 | | | | | x | | | o |
| Subject 2 | | | | | x, o | | | |
| Subject 3 | | | x, o | | | | | |
| Subject 4 | | | | | x | | | o |
| Subject 5 | | | | | | | x | o |
| Subject 6 | | | | | x, o | | | |
| Subject 7 | | | | | o | x | | |

Conclusion:

The results of this study showed a normalization of the hypersensitive gag reflex response when a pressure of 0.5-1.0 lbs was applied to the pressure point of the palm of either the right or left hand. In Table 1, all subjects showed a hypersensitive gag reflex response because all of them had gag reflex responses elicited at or before anterior faucial pillars. However, after the application of the pressure to the pressure point at the palm, all subjects, except subject 3 and subject 7, had gag reflex responses elicited at or after post faucial pillars 74, showing normal gag reflex responses. Although subjects 3 and 7 had gag reflex responses that were not normalized, the gag reflex response of subject 3 moved posteriorly from anterior to cheek at the baseline trial 71 to 12-year molars 72/anterior faucial pillars 73 after the pressure treatment; the gag reflex of subject 7 moved posteriorly from anterior faucial pillars 73 to post faucial pillars 74 during the pressure application to the left hand. Accordingly, all subjects showed a diminishing effect in their gag reflex responses during the pressure treatment to the marked pressure point.

Regarding the effective period after the ending of the pressure treatment, the two subjects' tests showed that the pressure treatment might remain effective even after, if within 15 to 30 minutes of, the ending of the pressure application. However, the example only used two subjects, and therefore more extensive research with a larger sample may be needed to study this effective period.

Example 3

This Example was an exploratory study to establish that the application of pressure to the pressure point using the hand pressure device of the present invention reduces the triggering of the gag reflex responses in healthy adults and to introduce a methodological approach to evaluate the gag reflex on the basis of the location of sensory stimulation in the oral cavity.

For the purpose of studying the effect of this invention on hypersensitive gag reflex responses in this example, a test sensor probe 18 and a data collection unit 19 (FIG. 1) were used to collect test data. However, the test probe 18 and the data collection unit 19 are not a part of the present invention.

Subjects:

All of subjects were college students with a self-perceived normal or hypersensitive gag reflex. All volunteers were screened for overt neurological difficulties. Forty-one subjects initially participated in the study. All subjects but two were Caucasian. In the baseline trials, five subjects (four women and one man) in the normal group were unable to continue the study after the baseline trials because no motor responses were observed with stimulation of the posterior pharyngeal wall at the baseline trials. Therefore, only thirty-six subjects proceeded to sham trials and treatment trials.

Subjects were placed into two groups according to baseline trial scores listed in Table 1. The hypersensitive group consisted of four women and three men with a mean age of eighteen point eight (18.8) years (standard deviation (SD)= 0.35). The normal (control) group consisted of twenty women and fourteen men with a mean age of twenty point zero (20.0) years (SD=2.65).

Procedure:

The subjects underwent a series of gag reflex response tests: baseline trials, sham trials and treatment trials. The test sensor probe 18 with a bend sensor potentiometer was used to record the amount of pressure applied to the anatomical structure that elicited the gag reflex response. As the probe contacted the inner surface of the oral cavity (FIG. 7), the probe bent the flexible sensor and generated a change in the output voltage, which was recorded by the data collection unit and then transferred to a desktop computer. The probe sensor had a light attached to the end for more accurate identification of the stimulated oral cavity structure.

Baseline Trials.

The purpose of the baseline trials was to establish a baseline data of gag reflex responses for all subjects. In the baseline trials, no treatment whatsoever was applied to the subjects. One gag reflex from the left side of a subject's oral cavity and one from the right side of the oral cavity were elicited using the test sensor probe 18 in a random order. Once a gag reflex response was elicited from the subject for that side of the oral cavity, the trial was stopped and no more posterior oral positions for that side of the oral cavity were tested for gag reflex response. During these two trials, the point in the mouth (the anatomical marker) at which each subject gagged was determined by means of a gag trigger point index (GTPI) and served as a baseline data for that subject. The GTPI was an ordinal index in which the oropharyngeal regions 70 were divided according to anatomical landmarks and assigned a score (an integer value from 0 to 8) (FIG. 1 and Table 1). All of the stimulation to elicit the gag reflexes began from a high GTPI area (an internal cheek 71) to a low GTPI area (a pharyngeal wall 75). To differentiate responses that occurred at the posterior pharyngeal wall (gag response elicited versus no motor response), two potential values of 1 to 0 were assigned. If a subject scored zeros for both sides of the intraoral cavity, the subject was excluded from any further trials. Five subjects (four women and one man) were thus excluded from any further trials because no motor responses were observed with stimulation of the posterior pharyngeal wall. Therefore, only thirty-six subjects proceeded to sham trials and treatment trials.

The baseline trials were also the sole determiner of group classification of normal versus hypersensitive for this example. The hypersensitive group included subjects who gagged at stimulation at or before the anterior faucial pillar region 73 (GTPI score≥6) on at least one side of the intraoral cavity. The other subjects were placed in the normal sensitivity group (normal group).

Sham Trials.

Figure 8:
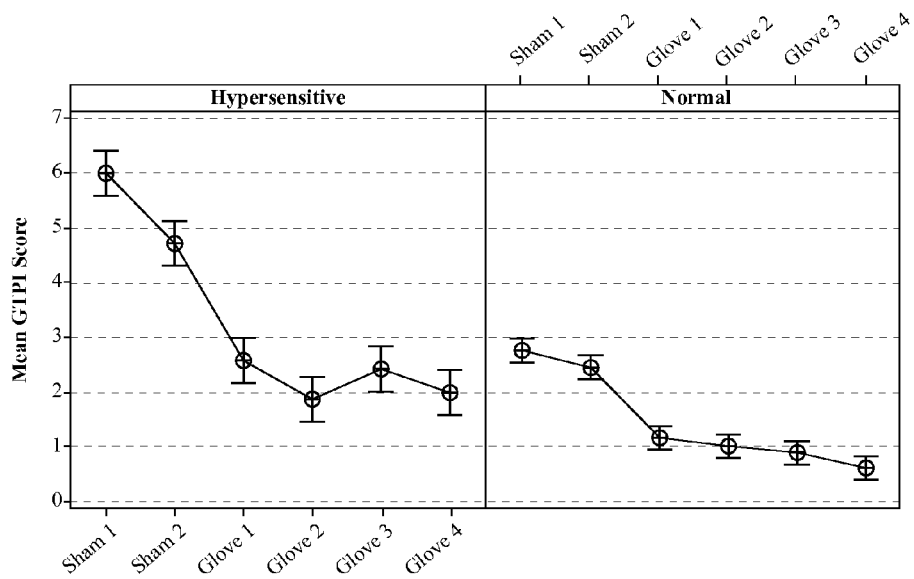
FIG. 8 is a graph illustrating treatment sequences versus mean gag trigger point index (GTPI) of a hypersensitive group and a normal group as described in example 3. It compares the mean GTPI scores of the hypersensitive group with that of the normal group to demonstrate the gag reflex response normalization or reduction capability of the present invention.

These trials were performed after the completion of the baseline trials. All subjects were told that they would be wearing over-the-counter anti-nausea bracelets that may be effective in minimizing the gag reflex response. An adjustable bracelet was fastened lightly around a randomly selected wrist. Two gag responses were elicited with one gag response from the left side of a subject's oral cavity and the other one from the right side of the oral cavity. The order in which a particular side of the oral cavity was stimulated was randomized. A break of at least one minute was provided between trials. The location of stimulation in the mouth where a gag was elicited was scored according to the GTPI as listed in Table 1. The results of the sham trials were compared to that of treatment trials as shown in FIG. 8.

Treatment Trials.

First, the pressure point 42 on a subject's palm was marked with a felt-tip marker as shown in FIG. 4. The pressure point 42 was located in the middle of the palm at the intersection of the thumb and the third finger. Then a randomly selected hand of a subject was inserted into the splint 10 of the present invention. The pressure actuator of the hand pressure device was then placed over the marked pressure point of the palm. The straps were fastened to secure the device. Once the device was secured, the subject was instructed not to resist the pressure applied to the hand when an investigator manually increased the force of the actuator to about 2 lbs.

Unlike the sham trials in which the subjects were led to believe that the light touch from the bracelet was effective for altering gag reflex, no information was given to the subjects about the effect of this pressure treatment. If a subject asked, an ambivalent response was given such as, "we're just trying it out."

While the pressure was applied to the pressure point of a subject's palm using the device of the present invention, a gag reflex response was elicited on either the right side of the intraoral cavity or the left side of the intraoral cavity. After eliciting the first gag reflex response from one side of the intraoral cavity, the hand pressure device was moved to the other hand. Then a second gag reflex response was elicited while a pressure was applied to the pressure point of the palm of the second hand using the device. Accordingly, a total of two gag reflex responses were elicited with one gag reflex response from each side of the intraoral cavity. The order in which a particular side of the oral cavity was stimulated was randomized. A break of at least one minute between trials was provided, which should have provided sufficient time for the strength of the gag reflex contraction to return to the baseline state (Jacob L, Gossman M. D., Neurology 1980, v. 30 (2), pp. 184-188). A longer break time was provided if a subject requested it.

The raw data gathered were analyzed by using a repeated-measure analysis of variance (ANOVA) of a mixed effect model fit to the experimental GTPI scores. All analysis was performed by using a preferred statistical software, PROC Mixed, Version 9.1 for Windows, SAS, Cary, N.C.). This type of statistical model allows for comparing effects of between-subject factors and within-subject factors while accommodating potential correlation among measurements made in the same subject. Between subject factors were group and gender factors. The group factor referred to hypersensitive or normal sensitivity group as established by the baseline trials. Within-subject factors were experimental treatment and stimulus side factors. The experimental treatment factor referred to sham trials, left hand pressure device trials and right hand pressure device trials. The stimulus side factor referred to left or right side of intraoral cavity.

sensitivity group, women had an overall mean GTPI score of 1.46 (SD=1.38) while men had an overall mean GTPI score of 1.52 (SD=1.31).

Tables 5 and 6 show that a significant treatment-group interaction effect was observed, indicating that the difference between mean GTPI response for the hypersensitivity group and normal sensitivity group was dependent on the treatment being used, such as sham, left hand pressure device, or right hand pressure device. Therefore, any assessment of group effects must be made according to the particular treatment.

TABLE 5

Descriptive GTPI data between hypersensitive and normal sensitivity groups (control) across baseline, sham, left hand pressure and right hand pressure gag treatments

| Group | Stimulus Side | Baseline Mean (SD) | Sham Mean (SD) | Left-hand Mean (SD) | Right-hand Mean (SD) |
|---|---|---|---|---|---|
| Hypersensitive (n = 7) | Right | 5.86 (1.70) | 5.86 (1.70) | 2.29 (1.70) | 2.57 (1.72) |
|  | Left | 5.71 (0.95) | 4.86 (1.10) | 1.71 (0.95) | 2.29 (1.60) |
| Normal sensitivity (n = 29) | Right | 3.07 (1.46) | 2.50 (1.32) | 0.96 (0.92) | 1.10 (0.86) |
|  | Left | 3.14 (1.33) | 2.72 (1.33) | 0.79 (0.68) | 0.83 (1.10) |

Results:

Between the baseline trials and the sham trials, no significant changes in mean GTPI score were found after adjusting for gender and stimulus side (F=0.81, numerator degrees of freedom=1, denominator df=33, P=0.3741). FIG. 7 illustrates the locations in the oral cavity where gag reflex can be elicited. Table 4 shows a corresponding baseline gag trigger point index (GTPI) score for each particular location in oral cavity where gag reflex can be elicited and a number of subjects whose gag reflex was elicited for that particular location.

TABLE 4

Description of baseline Gag Trigger Point Index (GTPI) Score coded by location in oral cavity where gag reflex response was elicited, with number of subjects in each category

| Location of Gag | Gag Trigger Point Index (GTPI) Score | N |
|---|---|---|
| Posterior Pharyngeal Wall, No motor response | 0 | 5 |
| Posterior Pharyngeal Wall, Motor response | 1 | 4 |
| Between Posterior Faucial Pillars/Posterior Pharyngeal Wall | 2 | 2 |
| Posterior Faucial Pillars | 3 | 6 |
| Between Anterior Faucial Pillars/Posterior Faucial Pillars | 4 | 11 |
| Anterior Faucial Pillars | 5 | 6 |
| Between $2^{nd}$ Molars/Anterior Faucial Pillars | 6 | 4 |
| $2^{nd}$ Molars | 7 | 3 |
| Internal cheek, center | 8 | 0 |

Repeated-measure ANOVA was then performed on the treatment trial data to investigate the effect of the pressure treatment on mean GTPI scores. The results are shown in Tables 5-7 and FIG. 8. No statistical significant change in mean GTPI score was found based on the stimulus side or the order in which a particular side of the oral cavity was stimulated. However, ANOVA results revealed a significant gender-group interaction for the hypersensitive group regardless of treatment while no gender-group interaction for the normal sensitivity group. In the hypersensitive group, women had an overall mean GTPI score of 2.58 (SD=2.12) while men had an overall mean GTPI score of 4.17 (SD=1.50). In the normal Table 7 uses statistical contrasts to illustrate the treatment effect in both hypersensitive and normal sensitivity group. No statistical significance was shown for the discrepancies between the groups in left hand pressure device and right hand pressure device trials. However, a statistically lower GTPI scores for treatment trial (P<0.05) was found for both groups.

TABLE 6

Repeated-Measures Analysis of Variance Test Results for Fixed Effects

| Effect | Numerator Degree of Freedom | Denominator Degree of Freedom | F-Value | P-Value |
|---|---|---|---|---|
| Stimulus Side of Oral Cavity | 1 | 32 | 3.57 | 0.0678 |
| Gender | 1 | 32 | 11.65 | 0.0018 |
| Treatment | 2 | 32 | 81.14 | <0.0001 |
| Group | 1 | 32 | 46.34 | <0.0001 |
| Gender/gender-Group Interaction | 1 | 32 | 11.72 | 0.0017 |
| Treatment-Group Interaction | 2 | 32 | 8.77 | 0.0009 |

TABLE 7

Hypersensitive vs. Normal Sensitivity Group discrepancies in Mean GTPI compared between pairs of experimental treatments. All P-values were Bonferroni adjusted.

| Pairwise treatment comparison | Numerator Degree of Freedom | Denominator Degree of Freedom | F-value | Adjusted P-value |
|---|---|---|---|---|
| Sham vs. Left Glove | 1 | 32 | 17.46 | 0.0006 |
| Sham vs. Right Glove | 1 | 32 | 12.20 | 0.0036 |
| Left Glove vs. Right Glove | 1 | 32 | 2.50 | 0.3705 |

FIG. 8 illustrates mean GTPI scores for both groups by order of application for that particular subject. The order of sham and treatment trials was randomized to reduce the effect of the subjects' expectation. FIG. 8 shows that for all subjects in both groups, the gag reflex responses moved posteriorly toward the pharyngeal wall after the application of pressure to the pressure point 42 on the subject's palm. Comparing the two groups, the subjects in the hypersensitive group showed a more statistically significant GTPI score change.

Conclusion:

The above results from FIG. 8 showed a significant posterior change in trigger point in the subjects of both the hypersensitive group and the normal sensitivity group after the application of pressure to the pressure point 42 on the palms using the present invention. A more significant change in trigger point was shown for the subjects in the hypersensitive group. Moreover, for the nine subjects in the normal sensitivity group reporting a self-perceived heightened gag reflex sensitivity during the initial interview, the palm pressure point treatment using the present invention was effective in reducing gag reflex responses for the nine subjects. This suggests that application of pressure to the pressure point of the palm (or the center of the palm) using the present application during dental procedures would make triggering a gag reflex response less likely.

A significant gender-group interaction in the hypersensitive group was found while no significant gender-group interaction for the normal sensitivity group was found. More specifically, it was observed that gag reflexes in the men of the hypersensitive group were stimulated significantly more anteriorly than that of the women in the hypersensitive group. It was not clear at this time why males in the hypersensitive group tended to react to more anterior stimulation and why this same gender difference is not seen in the normal sensitivity group.

This example also compares the effect of light touch from the sham trials and firm pressure from the treatment trials. Light touch was examined because in many people light touch follows a different neurological pathway from that of firm pressure. Moreover, at the skin level, different sensory receptors are responsible for transmitting light touch versus that for firm pressure. Specific neurological mechanisms are currently being explored. The results showed that comparing two types of touches, firm pressure using the present invention on the pressure point of the palm produced statistically lower GTPI scores than that of light touch from a bracelet at the wrist.

Furthermore, this significant difference between firm pressure in the treatment trials and the light touch in the sham trials shows that distraction caused by the firm pressure was not the reason that the subject's gag reflex response was diminished. If distraction were the cause of the change in a subject's gag reflex, it would show up in the sham trial where the subject was convinced that the light touch from the bracelet would change their gag reflex response. Moreover, if distraction were the underlying phenomenon that reduced the gag reflex response, the gag reflex response should have returned to the baseline values after repeated treatment trials as the subject become accustomed to the distractions associated with the procedures.

In addition, this significant difference between the treatment trials and the sham trials also showed that a potential order effect, fatiguing of the gag reflex with repeated stimulation, was not the cause of the gag reflex reduction. Moreover, the potential order effect was minimized by a randomization of the order of the treatment and sham trials.

After eliminating distraction and potential order effect as two possible causes of the gag reflex reduction, the results from the current example 3 showed that the firm pressure on the pressure point/region of the palm using the present invention would normalize the hypersensitive gag reflex response or might even diminish normal gag reflex responses.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A hand pressure device for diminishing a human user's gag reflex response, comprising:
   a. an enclosure having a dorsal member, a volar member, the volar member having a palm support region, a finger support region, and an opening in the palm support region; wherein the palm support region comprises at least one substantially rigid member adapted to immobilize a palm of the user;
   b. an actuating pressure system mounted on or in the opening of the palm support region so that the actuating pressure system is adjacent to a pressure region of the palm and is able to convert energy into linear motion to apply a pressure force consistently at about 1 lb or above to the pressure region of the palm, wherein the pressure region of the palm is a 1.0 inch generally circular region fading from each direction of a pressure point located at a middle of the palm at an intersection of two straight lines substantially perpendicular to each other, wherein one line extends from a middle of a volar distal edge of an intermediate phalange of a third finger to the middle of the palm and the other line extends from a volar center of a proximal phalange of a thumb to the middle of the palm; and
   c. a power supply connected to the actuating pressure system, wherein the power supply provides an electrical current to the actuating pressure system to enable the actuating pressure system to exert a consistent pressure to the pressure region of the palm only in order to diminish the user's gag reflex response.

2. A hand pressure device for diminishing a human user's gag reflex response, comprising:
   a. an enclosure having
      i. a dorsal member,
      ii. a volar member, the volar member having a palm support region and a finger support region, and
      iii. an opening in the palm support region, which is adjacent to a pressure region of the palm, wherein the pressure region is a 1.0 inch generally circular region fading from each direction of a pressure point located at a middle of the palm at an intersection of two straight lines substantially perpendicular to each other; wherein one line extends from a middle of a volar distal edge of an intermediate phalange of a third finger to the middle of the palm, and the other line extends from a volar center of a proximal phalange of a thumb to the middle of the palm;
   wherein the palm support region comprises at least one substantially rigid member adapted to immobilize the palm;
   b. an actuating pressure system having a pressure cylinder, wherein the actuating pressure system is mounted in the opening of the palm support region so that the pressure cylinder protrudes slightly out of the opening to convert energy into linear motion to apply a constant pressure directly on the pressure region of the palm, and the pressure is consistently at about 1 lb or above; and c. a power supply connected to the actuating pressure system, wherein the power supply provides an electrical current to the actuating pressure system to enable the actuating pressure system to exert a consistent pressure of about 1 lb or above to the pressure region of the palm only in order to diminish the user's gag reflex response.

3. The device according to claim 1, wherein the actuating pressure system is a voice coil actuating cylinder system, comprising a voice coil actuator attached to a pressure cylinder.

4. The device according to claim 3, wherein the enclosure is a splint adapted to conform to a palm region of the user's hand and to extend over at least one portion of the user's fingers, comprising:
   a. a volar member,
   b. a dorsal member, and
   c. an opening at the volar side of the volar member sized to allow the voice coil actuating cylinder system to be removably mounted in the opening wherein the pressure cylinder protrudes slightly out of the inner side of the volar member adjacent to the pressure region of the palm.

5. The device according to claim 1, further comprising a first strap adapted to at least partially immobilize the fingers and a second strap with a fastener system to conform the enclosure to a wrist or a lower portion of the hand to provide support to the enclosure.

6. The device according to claim 1, wherein the pressure region is a 0.5 inch general circular region fading from each direction of the pressure point.

7. The device according to claim 1, wherein the pressure region is the pressure point.

8. The device according to claim 3, wherein the voice coil actuator comprises a coil attached to the pressure cylinder, and a housing enclosing both the coil and the pressure cylinder, wherein the electrical current from the power source causes the housing to move relative to the fixed coil to enable the cylinder to exert pressure to the pressure region.

9. The device according to claim 8, wherein the voice coil actuator is a solenoid capable of converting electrical energy into linear motion so as to actuate the pressure cylinder.

10. The device according to claim 9, wherein the solenoid is capable of precise force control and being used in short stroke close loop servo applications.

11. The device according to claim 9, wherein the solenoid is capable of actuating a peak force of at least about 2 lbs.

12. The device according to claim 3, where the pressure cylinder is formed of plastic material.

13. The device according to claim 12, wherein the pressure cylinder is not more than 1.0 inch in length and not more than 1.2 inches in diameter.

14. A method of using a hand pressure device for diminishing gag reflex response, the method comprising:
   a. providing a hand pressure device comprising
      i. an enclosure surrounding at least a portion of a human user's hand, said enclosure having a palm support region with at least one substantially rigid member adapted to immobilize the user's palm;
      ii. an actuating pressure system mounted at an inner surface of a volar side of the enclosure, and the actuating pressure system is able to convert energy into linear motion to apply a constant pressure force at about 1 lb or above a pressure region of the palm, which a 1.0 inch generally circular region fading from each direction of a pressure point located at a middle of the palm at an intersection of two straight lines substantially perpendicular to each other, wherein one line extends from a middle of a volar distal edge of an intermediate phalange of a third finger to the middle of the palm and the other line extends from a volar center of a proximal phalange of a thumb to the middle of the palm; and
      iii. a power supply connected to the actuating pressure system, wherein the power supply provides an electrical current to the actuating pressure system to exert pressure to the pressure region of the palm in order to diminish the user's gag reflex response;
   b. disposing the hand pressure device onto a hand of a user;
   c. positioning the actuating pressure system against the pressure region of the palm;
   d. securing the hand pressure device to the hand, thereby immobilizing the palm region of the hand; and
   e. applying an electrical current to the actuating pressure system to exert pressure to the pressure region only and thereby diminish the user's gag reflex response.

15. The method according to claim 14, wherein the pressure region is the pressure point.

16. The method according to claim 14, wherein the step e further comprises increasing the pressure exerted onto the pressure region to at least about 2 lbs.

17. The method according to claim 14, further comprising a step of stopping the application of the force to the pressure region of the palm for fifteen to thirty minutes and then a subsequent step of reapplying an electrical current to the actuating pressure system to enable it to exert another pressure force on the pressure region.

18. A method of using a hand pressure device for diminishing gag reflex response, the method comprising:
   a. providing a hand pressure device comprising
      i. an enclosure for surrounding at least a portion of a human user's hand, said enclosure having a palm support region with at least one substantially rigid member adapted to immobilize the user's palm;
      ii. an actuating pressure system mounted at an inner surface of a volar side of the enclosure, and the actuating pressure system is able to convert energy into a linear motion to apply a constant pressure force at about 1 lb or above to a pressure region of the palm, which is a 1.0 inch generally circular region fading from each direction of a pressure point located at a middle of the palm at an intersection of two straight lines substantially perpendicular to each other, wherein one line extends from a middle of a volar distal edge of an intermediate phalange of a third finger to the middle of the palm and the other line extends from a volar center of a proximal phalange of a thumb to the middle of the palm; and
      iii. a power supply connected to the actuating pressure system, wherein the power supply provides an electrical current to the actuating pressure system to exert pressure to the pressure region of the palm in order to diminish the user's gag reflex response;
   b. positioning the actuating pressure system against the pressure region of the palm;
   c. mounting the actuating pressure system onto the inner side of the volar side of the enclosure adjacent to the pressure region of the palm;
   d. fitting the hand pressure device onto the hand;
   e. securing the hand pressure device to immobilize the palm region of the hand; and f. applying an electrical current to the actuating pressure system to exert pressure to the pressure region only so as to diminish the user's gag reflex response.

19. The method according to claim 18, wherein the pressure region is the pressure point.

20. The method according to claim 18, wherein the step f further comprises increasing the pressure exerted onto the pressure region to at least about 2 lbs.

21. The method according to claim 18, further comprising a step of stopping the application of the force to the pressure region of the palm for fifteen to thirty minutes and then a subsequent step of reapplying an electrical current to the actuating pressure system to enable it to exert another pressure force on the pressure region.

22. The device according to claim 2, wherein the solenoid is capable of actuating a peak force of at least about 2 lbs.

23. The device according to claim 2, wherein the pressure cylinder is not more than 1.0 inch in length and not more than 1.2 inches in diameter.

24. The device according to claim 2, further comprising a first strap adapted to at least partially immobilize the fingers and a second strap with a fastener system to conform the enclosure to a wrist or a lower portion of the hand to provide support to the enclosure.

25. The device according to claim 2, wherein the pressure region is a 0.5 inch general circular region fading from each direction of the pressure point.

* * * * *